US011253445B1

(12) United States Patent
Shepherd, Jr.

(10) Patent No.: US 11,253,445 B1
(45) Date of Patent: Feb. 22, 2022

(54) OXIDATIVE HAIR COLOR REMOVER IN TABLET OR PELLET FORM

(71) Applicant: Bright International, LLC, Coolidge, AZ (US)

(72) Inventor: Walter B. Shepherd, Jr., Coolidge, AZ (US)

(73) Assignee: Bright International, LLC, Coolidge, AZ (US)

( * ) Notice: Subject to any disclaimer, the term of this patent is extended or adjusted under 35 U.S.C. 154(b) by 0 days.

(21) Appl. No.: 16/804,885

(22) Filed: Feb. 28, 2020

(51) Int. Cl.
| | |
|---|---|
| *A61K 8/23* | (2006.01) |
| *A61K 8/02* | (2006.01) |
| *A61Q 5/08* | (2006.01) |
| *A61Q 5/10* | (2006.01) |
| *A61K 8/26* | (2006.01) |
| *A61K 8/27* | (2006.01) |
| *A61K 8/73* | (2006.01) |
| *A61K 8/24* | (2006.01) |

(52) U.S. Cl.
CPC ............... *A61K 8/23* (2013.01); *A61K 8/0216* (2013.01); *A61K 8/24* (2013.01); *A61K 8/26* (2013.01); *A61K 8/27* (2013.01); *A61K 8/731* (2013.01); *A61K 8/732* (2013.01); *A61K 8/733* (2013.01); *A61Q 5/08* (2013.01); *A61Q 5/10* (2013.01)

(58) Field of Classification Search
CPC . A61K 8/23; A61K 8/26; A61K 8/731; A61K 8/732; A61K 8/27; A61K 8/24; A61K 8/733; A61K 8/0216; A61Q 5/10; A61Q 5/08
See application file for complete search history.

(56) References Cited

U.S. PATENT DOCUMENTS

| | | | | |
|---|---|---|---|---|
| 3,679,347 A | * | 7/1972 | Brown | A61Q 5/065 8/428 |
| 5,098,598 A | * | 3/1992 | Sankey | C11D 3/3945 252/186.26 |
| 6,264,703 B1 | * | 7/2001 | Coope | A61K 8/23 8/401 |
| 9,248,080 B2 | | 2/2016 | Deconinck et al. | |
| 2005/0281773 A1 | * | 12/2005 | Wieland | C12N 9/54 424/70.14 |
| 2006/0078584 A1 | * | 4/2006 | Lightcap | C02F 1/722 424/405 |
| 2012/0305416 A1 | * | 12/2012 | Miyabe | A61Q 5/10 206/223 |
| 2017/0035683 A1 | * | 2/2017 | Shepherd, Jr. | A61K 8/23 |

FOREIGN PATENT DOCUMENTS

| | | |
|---|---|---|
| GN | 101828550 A | 9/2010 |
| NL | 6402464 A | 9/1965 |

OTHER PUBLICATIONS

Deconinck et al. (FR2975289A1 Machine Translation) (Year: 2011).*
Rondot et al. (FR2969923A1 Machine Translation) (Year: 2012).*
International Search Report dated Apr. 8, 2021 issued in connection with PCT Application No. PCT/US2021/020196.
Written Opinion of the International Searching Authority dated Apr. 8, 2021 issued in connection with PCT Application No. PCT/US2021/020196.
European Search Report, dated Jul. 28, 2020, issued in connection with corresponding European Patent Application No. 20164751.8.
Sonthipet, Sorawot et al., "Bactericidal and Virucidal Efficacies of Potassium Monopersulfate and its Application for nactivating Avian Influenza Virus on Virus-Spiked Clothes," The Journal of Veterinary Medical Science, Jan. 1, 2018, vol. 80, No. 4, pp. 568-573.

* cited by examiner

*Primary Examiner* — Quanglong N Truong
(74) *Attorney, Agent, or Firm* — Akerman LLP

(57) ABSTRACT

An oxidative composition for the removal of natural and/or synthetic color from keratinaceous fibers may include a pellet or tablet that when added to a sufficient quantity of a peroxide developer solution readily disperses. The composition may include a gas generating agent to facilitate breakdown and dispersion of the pellet or tablet. The composition added to the developer may be agitated to forms homogeneous cream-like mixture for application to keratinaceous fibers.

20 Claims, No Drawings

OXIDATIVE HAIR COLOR REMOVER IN TABLET OR PELLET FORM

TECHNOLOGY FIELD

The present disclosure is related to components for formulating keratinaceous fiber bleaching application mixtures or, more specifically, to oxidative components for mixing with developer solution to formulate such keratinaceous fiber bleaching application mixtures.

BACKGROUND

The bleaching of human keratinaceous fibers, particularly human hair, is accomplished by oxidative degradation of the melanin pigment in hair. This is generally accomplished by application of a two-component mixture in which the first component is an alkaline mixture containing a persulfate and the second component is an aqueous developer solution of hydrogen peroxide. The first component is an oxidative composition and generally includes one or more peroxygenated ingredients such as ammonium, sodium or potassium persulfates, perborates or percarbonates. At the time of use, the first component is combined with the second component and the mixture is subsequently agitated, usually using an application tool such as a brush, to form a cream-like fluid or slurry suitable for application to hair. This bleach mixture is then allowed to remain on the hair for a specified process time, which generally does not exceed 60 minutes. The hair is then rinsed with potable water and may be shampooed or subjected to further processing, such as coloring.

The first component is typically provided as a powdered mixture. Powdered mixtures of oxidizers, alkalis and other ingredients, however, are irritants to the respiratory system. When working with these powders, a portion of the powder particulates inevitably becomes airborne, risking aspiration of the irritant ingredients. These airborne particulates pose a potential hazard to individuals in proximity. Several compositions have addressed this issue by adding mineral oil or nonreactive oils, esters or similar fluids which coat or agglomerate the particles, thereby limiting the generation of airborne particulates during normal handling. U.S. Pat. No. 9,248,080 B2 describes a process whereby an oxidative composition is formed into a pellet or tablet by a compression process. Such dedusting processes are relatively effective in controlling airborne particulates. However, while compressing the oxidizer component may reduce airborne particulates, it may also create a number of issues unique to the compressed form.

SUMMARY

In one aspect, an oxidative composition for the removal of natural and/or synthetic color from keratinaceous fibers includes a pellet or tablet that when added to a sufficient quantity of a peroxide developer solution readily disperses and with agitation forms a homogeneous cream-like mixture for application to keratinaceous fibers.

In various embodiments, the pellet or tablet includes a gas generating agent to facilitate dissolution and/or dispersion of the pellet or tablet when added to the peroxide developer solution. The composition may include the gas generating agent in an amount between about 0.5% and about 80% by weight. In one formulation, the gas generating agent comprises potassium peroxymonosulfate (KMP), anhydrous sodium perborate (ASP), or combination thereof. For example, the gas generating agent may include potassium peroxymonosulfate (KMP) in an amount between about 0.5% and about 80% by weight of the composition. In a further or another example, the gas generating agent comprises anhydrous sodium perborate (ASP) alone or in combination with potassium peroxymonosulfate (KMP) in an amount between about 0.5% and about 80% by weight of the composition.

In any of the above or another embodiment, the composition may include at least one alkali persulfate selected from lithium persulfate, sodium persulfate, potassium persulfate, rubidium persulfate, cesium persulfate, ammonium persulfate, or combinations thereof. Alkali persulfate may be present in an amount between about 10% and about 80% by weight of the composition. In any of the above or another embodiment, the composition includes an alkaline agent selected from one or more water soluble Group IA, Group IIA, ammonia, aluminum or zinc silicates, carbonates, phosphates, and/or hydroxides. The composition may include between about 5% and about 45% by weight alkaline agent. In any of the above or another embodiment, the composition may include one or more rheological modifiers selected from one or more hydrophilic thickeners, amphiphilic polymers, synthetic polymers, natural or synthetic gums or ionic or nonionic derivates thereof, starches, modified starches, dextrins, sugars, polyhydric alcohols, cellulose, cellulose derivatives, natural or synthetic waxes or esters present in an amount between about 0.5% and about 25% by weight, individually or in combination. In any of the above or another embodiment, the composition includes a disintegration assisting agent selected from starches, starch glycolate, starch derivatives, alginic acids, alginic acid salts, cellulose, cellulose derivatives, mineral clays, hydrating clays, or combinations thereof present in an amount between about 0.5% and about 20% by weight, individually or in combination. In any of the above or another embodiment, the composition includes one or more surfactants and/or metallic soaps in an amount between about 0.5% and about 10% by weight. The one or more surfactants may be selected from one or more anionic surfactants, nonionic surfactants, amphoteric surfactants, or combinations thereof. The one or more metallic soaps may be selected from one or more alkali metal soaps including Group IA, Group IIA, aluminum, or zinc.

In another aspect, an oxidative composition for mixing with a peroxide developer solution to formulate a bleach mixture for removal of natural and/or synthetic color from keratinaceous fibers includes a peroxygenated ingredient and a gas generating agent, wherein the composition comprises a compressed tablet or pellet.

The composition may include the gas generating agent in an amount between about 0.5% and about 80% by weight. In one example, the gas generating agent is selected from potassium peroxymonosulfate (KMP), anhydrous sodium perborate (ASP), or combination thereof and is present in an amount between about 0.5% and about 80% by weight of the composition. In one embodiment, the one or more peroxygenated ingredients include at least one persulfate. In some embodiments, the persulfate comprises one or more alkali persulfates selected from lithium persulfate, sodium persulfate, potassium persulfate, rubidium persulfate, cesium persulfate, ammonium persulfate, or combinations thereof. The persulfate may be present in an amount between about 10% and about 80% by weight of the composition.

In various embodiments, the composition may include an alkaline agent selected from one or more water soluble Group IA, Group IIA, ammonia, aluminum or zinc silicates, carbonates, phosphates, and/or hydroxides in an amount between about 5% and about 45% by weight of the composition. In any of the above or another embodiment, the composition includes one or more rheological modifiers selected from one or more hydrophilic thickeners, amphiphilic polymers, synthetic polymers, natural or synthetic gums or ionic or nonionic derivates thereof, starches, modified starches, dextrins, sugars, polyhydric alcohols, cellulose, cellulose derivatives, natural or synthetic waxes or esters present in an amount between about 0.5% and about 25% by weight, individually or in combination. In any of the above or another embodiment, the composition includes a disintegration assisting agent selected from starches, starch glycolate, starch derivatives, alginic acids, alginic acid salts, cellulose, cellulose derivatives, mineral clays, hydrating clays, or combinations thereof present in an amount between about 0.5% and about 20% by weight, individually or in combination. In any of the above or another embodiment, the composition includes one or more surfactants and/or metallic soaps in an amount between about 0.5% and about 10% by weight. The one or more surfactants may be selected from one or more anionic surfactants, nonionic surfactants, amphoteric surfactants, or combinations thereof. The one or more metallic soaps may be selected from one or more alkali metal soaps including Group IA, Group IIA, aluminum, or zinc.

In still another aspect, a method of formulating a bleach mixture for removal of natural and/or synthetic color from keratinaceous fibers includes mixing any of the compositions described above with a peroxide developer solution to formulate a slurry, cream, or paste mixture.

In yet another aspect, a method of making an oxidative composition for mixing with a peroxide developer solution to formulate a bleach mixture for removal of natural and/or synthetic color from keratinaceous fibers includes combining a first powder comprising at least one persulfate with a second powder comprising a gas generating agent, and compressing the powders to form a tablet or pellet.

DESCRIPTION

Two-component mixtures for bleaching of keratinaceous fibers may include a first component comprising an alkaline powder mixture containing a persulfate, e.g., one or more peroxygenated ingredients such as Group 1 (lithium persulfate, sodium persulfate, potassium persulfate, rubidium persulfate, and cesium persulfate), or ammonium persulfates, perborates, or percarbonates, and a second component comprising an aqueous developer solution. The developer solution will typically be a peroxide solution, such as a hydrogen peroxide solution, but other developer solutions may be used. This first component may be referred to as a bleach or oxidative composition and the second component may be referred to as a developer solution or composition. As introduced above, the oxidative action of peroxygenated salts and peroxides are inefficient oxidizing agents in acidic media. Accordingly, alkalizing agent may be added to basify the media. The alkalizing agent may be chosen from water-soluble Group IA, Group IIA, ammonia, aluminum or zinc silicates, carbonates, phosphates, and/or hydroxides. In addition to providing an alkaline media, the alkalizing agent also causes hair cuticles to swell or open to facilitate the bleaching action.

To reduce risk of aspirating the irritant powder of the oxidizer, the powder may be compressed to form a tablet. However, while compressing the oxidizer powder into a tablet may reduce airborne particulates, it may also create a number of issues unique to such a compressed form. For example, solubility of the tablet in the developer is a primary concern and is generally more difficult as compared with an equal weight of loose or uncondensed powder. Among other things, this difficulty is due to a reduction in the ratio of the surface area to the weight of powder when in the compressed form; therefore, the powder mass does not wet as fast in the liquid developer and therefore dissolves slower. Additionally, since in most cases the ratio of powder to liquid developer is 1:1 to 1:3, there is very little excess liquid and the compressed form absorbs or imbibes the liquid by a wicking action prior to actual disintegration or dispersion. Binders added to the compressed form provide tensile strength to prevent crumbling and improve dimensional stability but often reduce wettability and increase disintegration time. The binders and/or disintegrants added to facilitate the dispersion of the tablet or pellet are not functional with respect to the bleaching process and therefore dilute or reduce the bleaching effectiveness on a weight for weight basis as compared with the powder composition. The above disadvantages notwithstanding, tablet or pelletized oxidizer is advantageous in that it is virtually dust free and eliminates the need for weighing or measuring the powdered portion of the bleach application mixture since the weight of individual tablets is predetermined and fixed. Additionally, the compressed product is conducive to easy and accurate inventory control at the point of use, such as a professional salon. The user can readily determine how many applications remain in the product package simply by counting the number of tablets rather than roughly estimating the weight or volume of bulk powder remaining in a container. The herein described compositions and methods may be utilized to overcome the above disadvantages of compressed oxidative compositions.

The present disclosure describes an oxidative composition and process of making and using the composition together with a developer solution to formulate an application mixture for removal of natural and synthetic color from keratinaceous fibers, such as human hair. The oxidative composition may be compressed into a tablet or pellet form, which may be referred to herein collectively as a tablet, that is formulated to rapidly crumble, disperse, and/or disintegrate when mixed with the developer composition.

In various embodiments, a composition for bleaching keratinaceous fibers includes an oxidative composition comprising a compressed powder. In one example, the oxidative composition may comprise one or more peroxygenated ingredients and a gas generating agent. In a further example, the oxidative composition comprises at least one persulfate and a gas generating agent. The persulfate may include one or more alkali persulfates. When combined with a suitable quantity of aqueous peroxide developer solution, the gas generating agent is configured to generate a gaseous decomposition product in the aqueous alkali. The gas generating agent may be formulated to function as a superdisintegrant to thereby facilitate rapid and generally complete crumbling, disintegration, and/or dispersion of the tablet when added the developer solution.

The gas generating agent may include one or more chemicals, molecular compounds, and/or reactants that generate gas in aqueous alkali solution. In some embodiments, the gas generating agent comprises between about 0.5% and about 80% by weight of the oxidative composition. For example, the oxidative composition may comprise between about 0.5% and about 5%, between about 5% and about 15%, between about 15% and about 25%, between about 25% and about 35%, between about 25% and about 55%, between about 35% and about 45%, between about 35% and about 65%, between about 45% and about 55%, between about 55% and about 65%, between about 65% and about 80%, such as greater than about 15%, greater than about 25%, greater than about 30%, or greater than about 40% gas generating agent by weight. In various embodiments, the gas generating agent comprises one or more gas generators selected from potassium peroxymonosulfate (KMP), anhydrous sodium perborate (ASP), or combination thereof, which may include derivatives. In various embodiments, the oxidative composition comprises a combination of ASP and KMP. In one example, KMP is present in a greater amount by weight than ASP. For instance, the oxidative composition may include between about 10% and about 50% by weight KMP and between about 3% and about 30% by weight ASP, wherein KMP represents a larger weight percentage of the oxidative composition. In another example, ASP is present in a greater amount by weight than KMP. For instance, the oxidative composition may include between about 10% and about 50% by weight ASP and between about 3% and about 30% by weight KMP, wherein ASP represents a larger weight percentage of the oxidative composition.

As introduced above, the oxidative composition may comprise one or more peroxygenated ingredients, such as one or more persulfates. In an exemplary embodiment, the oxidative composition includes one or more persulfates comprising one or more alkali persulfates selected from lithium persulfate, sodium persulfate, potassium persulfate, rubidium persulfate, cesium persulfate, ammonium persulfate, or combination thereof. In some embodiments, persulfate may be present in an amount between about 1% and about 85% by weight of the oxidative composition, more preferably between about 10% and about 80% by weight, individually or in combination.

The oxidative composition may include an alkaline agent. Exemplary alkali agent may include one or more water soluble Group IA, Group IIA, ammonia, aluminum or zinc silicates, carbonates, phosphates, and/or hydroxides. In various embodiments, alkaline agent may be present in an amount between 0% and about 60% by weight of the oxidative composition, more preferably between about 5% and about 45% by weight, individually or in combination.

In some embodiments, the oxidative composition may include one or more rheological modifiers. Rheological modifiers may be present in an amount between 0% and about 40% by weight of the oxidative composition, more preferably between about 0.5% and about 25% by weight, individually or in combination. In one example, the oxidative composition comprises one or more rheological modifiers selected from hydrophilic thickeners, amphiphilic polymers, synthetic polymers, natural or synthetic gums or ionic or nonionic derivates thereof, starches, modified starches or derivatives, dextrins, sugars, polyhydric alcohols, cellulose, cellulose derivatives, natural or synthetic waxes, esters, or combinations thereof.

The oxidative composition may comprise a disintegration assisting agent. In various embodiments, the disintegration assisting agent may be present in an amount between about 0% and about 40% by weight of the oxidative composition, more preferably between about 0.5% and about 20% by weight, individually or in combination. In one example, the oxidative composition includes a disintegration assisting agent selected from one or more of alginic acids, alginic acid salts, cellulose, cellulose derivatives, starches, starch glycolate, starch derivatives, modified starches, mineral clays, hydrating clays, or combinations thereof.

The oxidative composition may comprise one or more surfactants and/or soaps. In one example, the oxidative composition includes one or more surfactants and/or soaps selected from anionic surfactants, nonionic surfactants, amphoteric surfactants, metallic soaps including those of Group IA, Group IIA, aluminum, or zinc. In various embodiments, the oxidative composition comprises between about 0% and about 20% by weight surfactants and/or soaps, or more preferably between about 0.5% and about 10% by weight surfactants and/or soaps, individually or in combination.

The oxidative composition may also include other ingredients. For example, the oxidative composition may include various aesthetic additives such as fragrances and/or dyes.

In one example, the oxidative composition includes at least one gas generating agent and at least one alkali persulfate. The gas generating agent may be present in an amount between about 0.5% and about 80% by weight of the oxidative composition, or any other weight or weight range described herein, and the persulfate may be present in an amount between about 10% and about 80%. The gas generating agent may be selected from KMP, ASP, or combination thereof. The alkali persulfate may be selected from Group 1 persulfates (lithium persulfate, sodium persulfate, potassium persulfate, rubidium persulfate, and cesium persulfate), ammonium persulfate, or combinations thereof. In a further example, the oxidative composition includes an alkaline agent in an amount between about 5% and about 45% by weight, one or more rheological modifiers in an amount between about 0.5% and about 25% by weight, a disintegration assisting agent in an amount between about 0.5% and about 20% by weight, and/or one or more surfactants and/or soaps in an amount between about 0.5% and about 10% by weight. The alkali agent may be selected from water soluble Group IA, Group IIA, ammonia, aluminum or zinc silicates, carbonates, phosphates, and/or hydroxides. The one or more rheological modifiers may be selected from hydrophilic thickeners, amphiphilic polymers, synthetic polymers, natural or synthetic gums or ionic or nonionic derivates thereof, starches, modified starches, dextrins, sugars, polyhydric alcohols, cellulose, cellulose derivatives, natural or synthetic waxes, esters, or combinations thereof. The disintegration assisting agent may be selected from one or more alginic acids, alginic acid salts, cellulose, cellulose derivatives, starches, starch glycolate, other starch derivatives, mineral clays, hydrating clays, or combinations thereof. The one or more surfactants and/or soaps may be selected from one or more anionic surfactants, nonionic surfactants, amphoteric surfactants, metallic soaps including those of Group IA, Group IIA, aluminum, or zinc, or combinations thereof.

Various exemplary oxidative compositions according to the present disclosure are also listed below in Table 1. The oxidative compositions described herein are not intended to be limited by the examples provided in Table 1. In some embodiments, the oxidative composition comprises one or more of the listed example oxidative compositions wherein the identified ingredients are present in an amount within +/−10% of the listed percent composition. The listed oxidative compositions represent dry to slightly moist powders with a bland, characteristic odor. The ingredients were blended together to form a homogeneous powder mixture before compression. In some instances, it may be advantageous to grind or reduce the particle size of the ingredients of the powder mixture to enhance the dissolution or break-up of the powders when the tableted or pelletized composition is contacted with developer solution. Control of the overall particle size of the powders may also increase the dimensional strength and cosmetic appearance, such as surface texture, of the tablet or pellet. In various embodiments, an advantageous particle size is less than about 1 mm (18 mesh), or more advantageous less than about 800 um (20 mesh). However, larger partial sizes may be used.

TABLE 1

| | EXAMPLES (% BY WEIGHT) | | | | | | | |
|---|---|---|---|---|---|---|---|---|
| | 1 | 2 | 3 | 4 | 5 | 6 | 7 | 8 |
| POTASSIUM PERSULFATE | 30.0 | 30.0 | 29.0 | 29.0 | 30.0 | 30.0 | 35.0 | 35.0 |
| AMMONIUM PERSULFATE | 20.0 | 20.0 | 20.0 | 20.0 | 16.5 | 16.5 | 8.0 | 8.0 |
| SODIUM SILICATE | | | 20.0 | 20.0 | | | 20.0 | 20.0 |
| SODIUM MATASILICATE | 14.0 | 14.0 | | | 15.0 | 15.0 | 5.0 | 5.0 |
| GUAR GUM | 2.0 | 2.0 | 2.0 | 2.0 | 2.0 | 2.0 | 2.0 | 2.0 |
| SODIUM LAURYL SULFATE | 2.0 | 2.0 | 2.0 | 2.0 | 2.0 | 2.0 | 2.0 | 2.0 |
| MAGNESIUM STEARATE | 2.0 | 2.0 | 2.0 | 2.0 | 2.0 | 2.0 | 2.0 | 2.0 |
| PRIMOJEL | | | 5.0 | 5.0 | 2.5 | 2.5 | 3.5 | 3.5 |
| LACTOSE | 10.0 | 10.0 | 10.0 | 10.0 | 15.0 | 15.0 | 15.0 | 15.0 |
| MINERAL OIL | | | | | | | 2.5 | 2.5 |
| POTASSIUM PEROXYMONOSULFATE | 20.0 | 10.0 | 10.0 | 5.0 | 15.0 | 7.5 | 5.0 | 2.5 |
| ANHYDROUS SODIUM PERBORATE | | 10.0 | | 5.0 | | 7.5 | | 2.5 |
| | 100.0 | 100.0 | 100.0 | 100.0 | 100.0 | 100.0 | 100.0 | 100.0 |

In various embodiments, a method of making the oxidative composition may include combining the gas generating agent with any oxidative composition, including known oxidative compositions, or ingredients thereof for mixing with developer solution to formulate a keratinaceous fiber bleaching composition. In one example, the method includes combining at least one peroxygenated ingredient, such as one or more persulfates, and the gas generating agent in an amount described herein. In a further example, the method includes combining an alkaline agent, one or more rheological modifiers, a disintegration assisting agent, and/or one or more surfactants and/or soaps in an amount described herein. The method may also include compressing the resultant powder to form a tablet. The compression of the powder into a tablet or pelletized form may be accomplished through the use of commercially available tableting or pelletizing presses following procedures known by those skilled in the art.

A method of using the oxidative composition may include adding the compressed powder or tablet to developer solution. The developer solution may be alkaline but will typically be acidic, generally between pH 1.5 and pH 3.5 prior to addition of the oxidative composition. Upon mixing with the oxidative composition, the combined mixture will typically be alkaline, generally between pH 9 and pH 12. However, the dissolution of the oxidative composition described herein is applicable to acidic, neutral, or alkaline solutions and, thus, the teachings herein may be applied equally to such solutions if used for removal of color from keratinaceous fibers. When combined with a suitable amount of developer solution, the oxidative composition, including the gas generating agent, may readily disperse, break up, and/or disintegrate. The suitable amount of developer solution may vary but will be a sufficient volume of developer to facilitate the dissolving, disintegration or crumbling of the tablet forming the desire volume of application mixture, which preferably has a cream-like consistency. In some embodiments, the oxidative composition tablet is formulated to be mixed with developer solution at a weight ratio between about 1:1 to about 1:4, tablet to solution. In some embodiments, the amount of oxidative composition added will be greater than that of the developer solution used. In a preferred embodiment, the oxidative composition tablet is formulated to be mixed with developer solution at a 1:1 weight ratio. The weight of the tablet can vary by design considerations such as desired volume, consistency, texture, or other characteristics of application mixture. In one example, the weight of the tablet may vary between about 5 g and about 50 g, or more preferably between about 15 g and about 45 g for a typical single application. The method may further include agitating or mixing the combined mixture. Mixing may result in formation of a cream, slurry, or paste-like bleach application mixture. In a further example, the method includes applying the bleach application mixture to keratinaceous fibers to remove natural or synthetic coloring. In one example, the mixture of the oxidative composition and developer solution may be mixed to form a homogeneous cream. In various embodiments, the oxidative composition may comprise a tableted alkaline oxidative composition and the method includes adding the alkaline oxidative composition to a suitable quantity of aqueous developer, e.g., hydrogen peroxide solution, wherein the gas generating agent generates gas that rapidly and completely crumbles, disperses, and/or disintegrates the oxidative composition to readily mix, forming a cream-like bleach application mixture for application to keratinaceous fibers.

This specification has been written with reference to various non-limiting and non-exhaustive embodiments. However, it will be recognized by persons having ordinary skill in the art that various substitutions, modifications, or combinations of any of the disclosed embodiments (or portions thereof) may be made within the scope of this specification. Thus, it is contemplated and understood that this specification supports additional embodiments not expressly set forth in this specification. Such embodiments may be obtained, for example, by combining, modifying, or reorganizing any of the disclosed steps, components, elements, features, aspects, characteristics, limitations, and the like, of the various non-limiting and non-exhaustive embodiments described in this specification.

Various elements described herein have been described as alternatives or alternative combinations, e.g., in a list of selectable actives, ingredients, or compositions. It is to be appreciated that embodiments may include one, more, or all of any such elements. Thus, this description includes embodiments of all such elements independently and embodiments including such elements in all combinations.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an application of the described embodiments. Further, the use of a singular noun includes the plural, and the use of a plural noun includes the singular, unless the context of the usage requires otherwise. Additionally, the grammatical conjunctions "and" and "or" are used herein according to accepted usage. By way of example, "x and y" refers to "x" and "y". On the other hand, "x or y" refers to "x", "y", or both "x" and "y", whereas "either x or y" refers to exclusivity.

Any numerical range recited herein includes all values and ranges from the lower value to the upper value. For example, if a concentration range is stated as 1% to 50%, it is intended that values such as 2% to 40%, 10% to 30%, 1% to 3%, or 2%, 25%, 39% and the like, are expressly enumerated in this specification. These are only examples of what is specifically intended, and all possible combinations of numerical values and ranges between and including the lowest value and the highest value enumerated are to be considered to be expressly stated in this application. Numbers modified by the term "about" are intended to include+/−10% of the number modified.

The present disclosure may be embodied in other forms without departing from the spirit or essential attributes thereof and, accordingly, reference should be had to the following claims rather than the foregoing specification as indicating the scope of the invention. Further, the illustrations of arrangements described herein are intended to provide a general understanding of the various embodiments, and they are not intended to serve as a complete description. Many other arrangements will be apparent to those of skill in the art upon reviewing the above description. Other arrangements may be utilized and derived therefrom, such that logical substitutions and changes may be made without departing from the scope of this disclosure.

What is claimed is:

1. An oxidative composition for mixing with a peroxide developer solution to formulate a bleach mixture for removal of natural and/or synthetic color from keratinaceous fibers, the composition comprising:
   an oxidizing agent comprising one or more persulfates;
   an alkaline agent; and
   a gas generating agent comprising potassium peroxymonosulfate (KMP), anhydrous sodium perborate (ASP), or combination thereof,
   wherein the composition is alkaline and has a tablet or pellet form that when mixed with a peroxide developer solution breaks-up to formulate a bleach mixture suitable for removal of natural and/or synthetic color from keratinaceous fibers.

2. The composition of claim 1, wherein the composition comprises the gas generating agent in an amount between about 0.5% and about 80% by weight.

3. The composition of claim 1, wherein the composition comprises between about 0.5% and about 80% by weight potassium peroxymonosulfate (KMP).

4. The composition of claim 1, wherein the composition comprises between about 0.5% and about 80% by weight anhydrous sodium perborate (ASP).

5. The composition of claim 1, wherein the persulfate comprises one or more alkali persulfates selected from lithium persulfate, sodium persulfate, potassium persulfate, rubidium persulfate, cesium persulfate, ammonium persulfate, or combinations thereof.

6. The composition of claim 5, wherein the composition comprises between about 10% and about 80% by weight persulfate.

7. The composition of claim 1, wherein the alkaline agent is selected from one or more water soluble Group IA, Group IIA, ammonia, aluminum or zinc silicates, carbonates, phosphates, and/or hydroxides.

8. The composition of claim 7, wherein the composition comprises between about 5% and about 45% by weight alkaline agent.

9. The composition of claim 1, further comprising one or more rheological modifiers selected from one or more hydrophilic thickeners, amphiphilic polymers, synthetic polymers, natural or synthetic gums or ionic or nonionic derivates thereof, starches, modified starches, dextrins, sugars, polyhydric alcohols, cellulose, cellulose derivatives, natural or synthetic waxes, esters, or combinations thereof in an amount between about 0.5% and about 25% by weight, individually or in combination.

10. The composition of claim 1, further comprising a disintegration assisting agent selected from starches, starch glycolate, starch derivatives, alginic acids, alginic acid salts, cellulose, cellulose derivatives, mineral clays, hydrating clays, or combinations thereof in an amount ranging from about 0.5% to about 20% by weight, individually or in combination.

11. The composition of claim 1, further comprising one or more surfactants and/or metallic soaps in an amount between about 0.5% and about 10% by weight, wherein the one or more surfactants are selected from one or more anionic surfactants, nonionic surfactants, amphoteric surfactants, or combinations thereof, and wherein the one or more metallic soaps are selected from one or more alkali metal soaps including Group IA, Group IIA, aluminum, or zinc.

12. A method of making an oxidative composition for mixing with a peroxide developer solution to formulate a bleach mixture for removal of natural and/or synthetic color from keratinaceous fibers, the method comprising:
   forming a tablet or pellet from an alkaline powder mixture, wherein the alkaline powder mixture comprises:
      an oxidizing agent comprising at least one persulfate;
      an alkaline agent; and
      a gas generating agent comprising potassium peroxymonosulfate (KMP), anhydrous sodium perborate (ASP), or combination thereof,
   wherein, when mixed with a peroxide developer solution, the tablet or pellet breaks-up to formulate a bleach mixture suitable for removal of natural and/or synthetic color from keratinaceous fibers.

13. The method of claim 12, wherein the gas generating agent is present in an amount between about 0.5% and about 80% by weight of the tablet or pellet.

14. The method of claim 12, wherein the potassium peroxymonosulfate (KMP) is present in an amount between about 0.5% and about 80% by weight of the tablet or pellet.

15. The method of claim 12, wherein the anhydrous sodium perborate (ASP) is present in an amount between about 0.5% and about 80% by weight of the tablet or pellet.

16. The method of claim 12, wherein the persulfate comprises one or more alkali persulfates selected from lithium persulfate, sodium persulfate, potassium persulfate, rubidium persulfate, cesium persulfate, ammonium persulfate, or combinations thereof, and wherein the persulfate is present in an amount between about 10% and about 80% by weight of the tablet or pellet.

17. The method of claim 16, alkaline agent powder with the first and second powders, wherein the alkaline agent selected from one or more water soluble Group IA, Group IIA, ammonia, aluminum or zinc silicates, carbonates, phosphates, and/or hydroxides, and wherein the alkaline agent is present in an amount between about 5% and about 45% by weight of the tablet or pellet.

18. The method of claim 16, wherein the alkaline powder mixture further comprises at least one of:
- one or more rheological modifiers selected from one or more hydrophilic thickeners, amphiphilic polymers, synthetic polymers, natural or synthetic gums or ionic or nonionic derivates thereof, starches, modified starches, dextrins, sugars, polyhydric alcohols, cellulose, cellulose derivatives, natural or synthetic waxes, esters, or combinations thereof in an amount between about 0.5% and about 25% by weight, individually or in combination;
- a disintegration assisting agent selected from starches, starch glycolate, starch derivatives, alginic acids, alginic acid salts, cellulose, cellulose derivatives, mineral clays, hydrating clays, or combinations thereof in an amount ranging from about 0.5% to about 20% by weight, individually or in combination; or
- one or more surfactants and/or metallic soaps in an amount between about 0.5% and about 10% by weight, wherein the one or more surfactants are selected from one or more anionic surfactants, nonionic surfactants, amphoteric surfactants, or combinations thereof, and wherein the one or more metallic soaps are selected from one or more alkali metal soaps including Group IA, Group IIA, aluminum, or zinc.

19. The composition of claim 1, wherein, when between about 15 g and about 45 g of the composition is mixed at a 1:1 weight ratio with a peroxide developer solution having a pH between 1.5 and 3.5, the resulting bleach mixture has a pH between 9 and 12.

20. The method of claim 12, wherein, when between about 15 g and about 45 g of the alkaline powder mixture formed into the tablet or pellet is mixed at a 1:1 weight ratio with a peroxide developer solution having a pH between 1.5 and 3.5, the resulting bleach mixture has a pH between 9 and 12.

* * * * *